the present invention relates to aminoacrylates which have a viscosity of 200 to 3000 mPa.s at 23° C. and 100% solids, a content of olefinic double bonds (calculated as C=C, molecular weight= 24) of 8 to 20% by weight and a nitrogen content of 0.4 to 2.0% by weight, and which are prepared by an addition reaction by reacting at a molar ratio of primary amino groups from component a) to olefinic double bonds from component b) of 0.05:1 to 0.25:1

United States Patent [19]

Meixner et al.

[11] Patent Number: 5,482,649
[45] Date of Patent: Jan. 9, 1996

[54] AMINOACRYLATES AND A PROCESS FOR THEIR PREPARATION

[75] Inventors: Jürgen Meixner, Krefeld; Wolfgang Fischer, Meerbusch; Christian Zwiener, Cologne, all of Germany

[73] Assignee: Bayer Aktiengesellschaft, Leverkusen, Germany

[21] Appl. No.: 95,886

[22] Filed: Jul. 22, 1993

[30] Foreign Application Priority Data

Aug. 5, 1992 [DE] Germany .......................... 42 25 921.5

[51] Int. Cl.$^6$ ....................................... C09K 3/00
[52] U.S. Cl. .................. 252/182.18; 252/183.11; 252/182.24; 252/182.27; 252/182.28; 525/10; 525/104
[58] Field of Search ......................... 252/182.24, 182.27, 252/182.28, 183.11; 522/104; 525/10, 104

[56] References Cited

U.S. PATENT DOCUMENTS

| | | | |
|---|---|---|---|
| 3,844,916 | 10/1974 | Gaske | 204/159.16 |
| 3,914,165 | 10/1975 | Gaske | 204/159.15 |
| 3,925,349 | 12/1975 | Gaske | 204/159.15 |

FOREIGN PATENT DOCUMENTS

| | | |
|---|---|---|
| 231442 | 8/1987 | European Pat. Off. . |
| 3706355 | 9/1988 | Germany . |
| 3836370 | 5/1990 | Germany . |

OTHER PUBLICATIONS

Houben Weyl, vol. 11/1, pp. 277 et seq., 1957.

*Primary Examiner*—Donald P. Walsh
*Assistant Examiner*—John R. Hardee
*Attorney, Agent, or Firm*—Joseph C. Gil; Thomas W. Roy; Richard E. L. Henderson

[57] ABSTRACT

The present invention relates to aminoacrylates which have a viscosity of 200 to 3000 mPa.s at 23° C. and 100% solids, a content of olefinic double bonds (calculated as C=C, molecular weight= 24) of 8 to 20% by weight and a nitrogen content of 0.4 to 2.0% by weight, and which are prepared by an addition reaction by reacting at a molar ratio of primary amino groups from component a) to olefinic double bonds from component b) of 0.05:1 to 0.25:1 a) mono- or diamines having a molecular weight of 31 to 300 and having aliphatically bound amino groups with b) acrylic esters of polyhydric alcohols which have been prepared at a COOH/OH equivalent ratio of 0.8:1 to 1:1 from b1) acrylic acid and b2) ether-alcohols which have 3 or 4 hydroxyl groups and a molecular weight of 136 to 1000, possess at least one ethylene oxide unit —$CH_2$—$CH_2$—O— as part of the ether structure and do not contain propylene oxide units —$CH_2$—$CH(CH_3)$—O—.

The present invention also relates to a process for the preparation these aminoacrylates.

4 Claims, No Drawings

AMINOACRYLATES AND A PROCESS FOR THEIR PREPARATION

BACKGROUND OF THE INVENTION

1. Field of the Invention

The invention relates to new aminoacrylates and a process for their preparation by the addition of primary mono- or diamines with aliphatically bound amino groups to acrylic esters of ethoxylated 3- or 4-hydric alcohols.

2. Description of the Prior Art

It is known that compounds which can be cured rapidly and completely by radiation, even in the presence of air, (DE-OS 2,346,424, DE-OS 3,706,355) are produced by the addition of a deficiency of primary or secondary amines to unsaturated polyacrylates, this proceeding in the same way as a Michael addition (Houben Weyl, vol. 11/1, p. 277 et seq., 1957).

Even though DE-OS 2,346,424 provides general information on the structure of such aminoacrylates, DE-OS 3,706,355 is restricted to aminoacrylates made from primary monoamines and acrylic esters. However, none of the references mentioned refer to low viscosity products with particularly high reactivities during radiation curing procedures.

An object of the present invention was to provide products having a viscosity (100% solids, 23° C.) of at most 3000 mPa.s, which permit particularly rapid curing when irradiated.

This object may be achieved with the aminoacrylates according to the invention which are described in more detail in the following along with the process for their preparation. It is an essential factor of the invention that to achieve the stated object, only special acrylates of the type described in more detail in the following are suitable as reactants for the addition of primary mono- or diamines.

SUMMARY OF THE INVENTION

The present invention relates to aminoacrylates which have a viscosity of 200 to 3000 mPa.s at 23° C. and 100% solids, a content of olefinic double bonds (calculated as C=C, molecular weight=24) of 8 to 20% by weight and a nitrogen content of 0.4 to 2.0% by weight, and which are prepared by an addition reaction by reacting at a molar ratio of primary amino groups from component a) to olefinic double bonds from component b) of 0.05:1 to 0.25:1 a) mono- or diamines having a molecular weight of 31 to 300 and having aliphatically bound amino groups with b) acrylic esters of polyhydric alcohols which have been prepared at a COOH/OH equivalent ratio of 0.8:1 to 1:1 from b1) acrylic acid and b2) ether-alcohols which have 3 or 4 hydroxyl groups and a molecular weight of 136 to 1000, possess at least one ethylene oxide unit —$CH_2$—$CH_2$—O— as part of the ether structure and do not contain propylene oxide units —$CH_2$—$CH(CH_3)$—O—.

The present invention also relates to a process for the preparation these aminoacrylates by an addition reaction by reacting at a molar ratio of primary amino groups from component a) to olefinic double bonds from component b) of 0.05:1 to 0.25:1 a) mono- or diamines having a molecular weight of 31 to 300 and having aliphatically bound primary amino groups with b) acrylic esters of polyhydric alcohols which have been prepared at a COOH/OH equivalent ratio of 0.8:1 to 1:1 from b1) acrylic acid and b2) ether-alcohols which have 3 or 4 hydroxyl groups and a molecular weight of 136 to 1000, possess at least one ethylene oxide unit —$CH_2$—$CH_2$—O— as part of the ether structure and do not contain propylene oxide units —$CH_2$—$CH(CH_3)$—O—.

DETAILED DESCRIPTION OF THE INVENTION

Component a) includes primary mono- or diamines having a molecular weight of 31 to 300, preferably 45 to 250, and having aliphatically bound primary amino groups. Monoamines are preferred to diamines. Examples of these amines include monoamines such as methylamine, n-butylamine, n-hexylamine, 2-ethylhexylamine, cyclohexylamine, ethanolamine and benzylamine; and diamines such as ethylene diamine, the isomeric diaminobutanes, the isomeric diaminohexanes and 1,4-diamino-cyclohexane.

Component b) includes reaction products which possess ester groups and are prepared from b1) acrylic acid and b2) 3- or 4-hydric alcohols which possess ether groups. The reaction of components b1) and b2) takes place while maintaining a molar ratio of carboxyl groups to hydroxyl groups of 0.8:1 to 1:1.

Suitable polyhydric alcohols b2) are those which have have 3 or 4 alcoholic hydroxyl groups, a molecular weight of 136 to 1000 and possess at least one ethylene oxide unit —$CH_2$—$CH_2$—O— as part of an ether structure. These of ether-alcohols may be obtained by the ethoxylation of suitable starter molecules in known manner. Suitable starter molecules include 3- or 4-hydric alcohols with no ether groups such as glycerine, trimethylolpropane, trimethylolethane, pentaerythritol and any mixture these and other polyhydric alcohols.

The ether-alcohols which are generally used possess a degree of ethoxylation of 1 to 10, preferably 2 to 8. The degree of ethoxylation is the number of moles of ethylene oxide which on average have been added onto 1 mole of the alcohol starter molecule. Particularly preferred are ethoxylated 3- or 4-hydric alcohols which have a degree of ethoxylation of 3 to 6 and a molecular weight of 224 to 400.

The alcohols b2) which possess ether groups are substantially free from propylene oxide units —$CH_2$—$CH(CH_3)$—O—. This means that during the alkoxylation reaction at most only small amounts of propylene oxide may be present (molar ratio of ethylene oxide to propylene oxide of at least 5:1). Otherwise, the properties of the aminoacrylates which are desired according to the invention cannot be achieved. Most preferably, component b2) exclusively contains ethoxylation products of the previously mentioned starter molecules.

The reaction products b) which possess ester groups also contain at least 10% by weight of olefinic double bonds (calculated as C=C, molecular weight=24).

The reaction between starting components a) and b) may take place in bulk or in the presence of suitable solvents such as ethyl acetate or toluene. The reaction temperature is generally 10° to 100° C., preferably 20° to 60° C. To perform the reaction in accordance with one embodiment according to the invention, component b) containing ester groups is initially introduced, optionally dissolved in an inert solvent of the type mentioned. The amine component a) is then added with stirring and the reaction mixture is stirred until the evolution of heat due to the exothermic addition reaction can no longer be detected. In the event that inert solvents are used, these may be removed if desired by distillation after the reaction.

Amine component a) is added in an amount such that the reaction product has a nitrogen content of 0.4 to 2.0% by weight. In general, this amount corresponds to a molar ratio of amino groups from component a) to olefinic double bonds from component b) of 0.05:1 to 0.25:1. The reaction products prepared in this way have a proportion of olefinic double bonds (calculated as C=C, molecular weight=24) of 8 to 20%, preferably 10 to 18% by weight, and a viscosity of 200 to 3000, preferably 300 to 2000 mPa.s at 23° C.

If required, one or more polymerization inhibitors may be added when performing the reaction, in order to prevent undesired polymerization of the reaction mixture. Suitable inhibitors include phenols such as 2,6-di-tert-butyl-p-cresol and hydroquinones such as the isomeric methylhydroquinones or phenothiazine.

The aminoacrylates obtained according to the invention represent valuable binders for coating compositions which can be radiation cured. When used in UV-curable compositions, photo-initiators must be added. Examples of these photoinitiators include benzophenone, benzoin and benzoin ether as well as benzil ketals and hydroxyalkylphenones. They are generally added in concentrations of 0.1 to 5% by weight.

Other ionizing types of radiation such as electron beams may also be used.

In the following examples all parts and percentages are by weight unless otherwise indicated.

EXAMPLES

Acrylic esters b)

The amount of alcohol and acrylic acid set forth in Table 1, 1.5% of p-toluene sulphonic acid as catalyst, and 0.1% of p-methoxyphenol and 0.1% of 3,4-di-tert.-butylhydroquinone as inhibitors (all percentages based on the total weight of alcohol and acrylic acid) were dissolved to provide a 70% solution in toluene. The mixture was heated to 100° to 120° C., while air was passed through and the water produced was continually removed by azeotropic distillation, until water no longer separated out. After cooling, the solvent was distilled off under vacuum at 50° to 90° C.

Aminoacrylates

The amount of amine a) set forth in Table 2 was added to the amount of acrylic ester b) set forth in Table 2 at 60° C. The mixture was held at 60° C. for 5 hours and then cooled.

Examples 1 to 5 were according to the invention.

In comparison example 6 acrylic ester bd) was used. Ester bd) was prepared using a COOH/OH equivalent ratio which was less than the required lower limit of 0.8:1.

In comparison example 7 the amount olefinic double bonds was less than the amount required by the present invention.

In comparison example 8 a propoxylated ether-alcohol bf) was used instead of an ethoxylated ether-alcohol.

In Comparison example 9 the alcohol bg) did not contain an ether structure.

COMPARISON EXAMPLE 10

Example 2 of DE-OS 3,706,355 was repeated. This example was directed to an adduct prepared from ethanolamine and a polyether acrylate. The polyether acrylate was obtained by initially preparing a polyether by alkoxylating trimethylolpropane with a mixture of ethylene oxide and propylene oxide (molar ratio of ethylene oxide:propylene oxide=1:2.5) and then reacting the polyether with acrylic acid. Viscosity (23° C./mPa.s): 550 mPa.s C=C double bond content: 12.0% Nitrogen content: 0.24%.

TABLE 1

| Acrylic esters b) | ba | bb | bc | bd | be | bf | bg |
|---|---|---|---|---|---|---|---|
| Alcohol b2) (mol) | | | | | | | |
| 3-fold ethoxylated glycerine | 1.0 | | | | | | |
| 4-fold ethoxylated trimethylolpropane | | 1.0 | | 1.0 | | | |
| 4-fold ethoxylated pentaerythritol | | | 1.0 | | | | |
| 12-fold ethoxylated trimethylolpropane | | | | | 1.0 | | |
| 3-fold propoxylated trimethylolpropane | | | | | | 1.0 | |
| trimethylolpropane | | | | | | | 1.0 |
| Acrylic acid b1) (mol) | 2.5 | 2.5 | 3.7 | 2.3 | 2.5 | 3.0 | 3.0 |
| COOH/OH ratio | 0.83:1 | 0.83:1 | 0.92:1 | 0.76:1 | 0.83:1 | 1:1 | 1:1 |
| Viscosity (mPa.s/23° C.) | 150 | 160 | 140 | 170 | 200 | 90 | 100 |

TABLE 2

| Starting materials (%) | Examples according to the invention | | | | | Comparison examples | | | |
| --- | --- | --- | --- | --- | --- | --- | --- | --- | --- |
| | 1 | 2 | 3 | 4 | 5 | 6 | 7 | 8 | 9 |
| Acrylic esters | | | | | | | | | |
| ba | 97.5 | — | — | — | — | — | — | — | — |
| bb | — | 97.4 | 96.6 | — | 94.6 | — | — | — | — |
| bc | — | — | — | 96.6 | — | — | — | — | — |
| bd | — | — | — | — | — | 96.6 | — | — | — |
| be | — | — | — | — | — | — | 97.5 | — | — |
| bf | — | — | — | — | — | — | — | 96.6 | — |
| bg | — | — | — | — | — | — | — | — | 96.6 |
| Ethanolamine | 2.5 | 2.6 | 3.4 | 3.4 | — | 3.4 | 2.5 | 3.4 | 3.4 |
| Cyclohexylamine | | | | | 5.4 | | | | |
| Viscosity (mPa.s/23° C.) | 550 | 440 | 780 | 630 | 570 | 1400 | 1700 | 520 | 540 |
| Olefinic double bonds (%) (MW = 24) | 16.3 | 13.2 | 13.1 | 15.3 | 12.9 | 12.4 | 7.3 | 14.8 | 23.5 |
| Nitrogen content (%) | 0.6 | 0.6 | 0.8 | 0.8 | 0.8 | 0.8 | 0.6 | 0.8 | 0.8 |

Application example The aminoacrylates from examples 1 to 5 and comparison examples 6 to 10 were each treated with 6.5 parts of Esacure TZT (trimethylbenzophenone, isomeric mixture, commercial product from Fratelli Lamberti). After applying the coating composition to cardboard (250 g/m²), they were passed under a Hanoviastrahler (80 W/cm, 10 cm distance). At a belt conveyer speed of 70 m/min, solvent resistant coatings were only produced with the examples according to the invention. The coatings from the comparison examples remained tacky.

Solvent resistant means that the coatings remained unchanged after at least 20 double wipes with a cloth soaked in butyl acetate under a load of 1 kg.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An aminoacrylate which has a viscosity of 200 to 3000 mPa.s at 23° C. and 100% solids, a content of olefinic double bonds (calculated as C=C, molecular weight=24) of 8 to 20% by weight and a nitrogen content of 0.4 to 2.0% by weight, and which is prepared by an addition reaction by reacting at a molar ratio of primary amino groups from component a) to olefinic double bonds from component b) of 0.05:1 to 0.25:1 a) mono- or diamines having a molecular weight of 31 to 300 and having aliphatically bound amino groups with b) acrylic esters of polyhydric alcohols which have been prepared at a COOH/OH equivalent ratio of 0.8:1 to 1:1 from b1) acrylic acid and b2) ether-alcohols which have 3 or 4 hydroxyl groups and a molecular weight of 136 to 1000, possess at least one ethylene oxide unit —CH$_2$—CH$_2$—O— as part of the ether structure and are substantially free from propylene oxide units —CH$_2$—CH(CH$_3$)—O—.

2. The aminoacrylate of claim 1 wherein component a) comprises a monoamine.

3. A process for the preparation of an aminoacrylate which has a viscosity of 200 to 3000 mPa.s at 23° C. and 100% solids, a content of olefinic double bonds {calculated as C=C, molecular weight=24) of 8 to 20% by weight and a nitrogen content of 0.4 to 2.0% by weight, by an addition reaction which comprises reacting at a molar ratio of primary amino groups from component a) to olefinic double bonds from component b) of 0.05:1 to 0.25:1 a) a mono- or diamine having a molecular weight of 31 to 300 and having aliphatically bound primary amino groups with b) an acrylic ester of a polyhydric alcohol which have been prepared at a COOH/OH equivalent ratio of 0.8:1 to 1:1 from b1) acrylic acid and b2) ether-alcohols which have 3 or 4 hydroxyl groups and a molecular weight of 136 to 1000, possess at least one ethylene oxide unit —CH$_2$—CH$_2$—O— as part of the ether structure and do not contain propylene oxide units —CH$_2$—CH(CH$_3$)—O—.

4. The process of claim 3 wherein component a) comprises a monoamine.

* * * * *